United States Patent [19]

Rutt

[11] Patent Number: 4,672,649

[45] Date of Patent: * Jun. 9, 1987

[54] THREE DIMENSIONAL SCANNED PROJECTION RADIOGRAPHY USING HIGH SPEED COMPUTED TOMOGRAPHIC SCANNING SYSTEM

[75] Inventor: Brian K. Rutt, San Francisco, Calif.

[73] Assignee: Imatron, Inc., South San Francisco, Calif.

[*] Notice: The portion of the term of this patent subsequent to Feb. 25, 2003 has been disclaimed.

[21] Appl. No.: 615,067

[22] Filed: May 29, 1984

[51] Int. Cl.$^4$ .............................................. A61B 6/02
[52] U.S. Cl. ...................................... 378/10; 378/41
[58] Field of Search ............... 378/10, 41, 99, 901, 378/19, 12, 4; 358/111

[56] References Cited

U.S. PATENT DOCUMENTS

| | | | |
|---|---|---|---|
| 3,432,657 | 3/1969 | Slavin | 378/41 |
| 4,075,492 | 2/1978 | Boyd et al. | 378/7 |
| 4,149,082 | 4/1979 | Haendle et al. | 378/41 |
| 4,158,142 | 6/1979 | Haimson | 378/10 |
| 4,214,267 | 7/1980 | Roese et al. | 378/99 |
| 4,352,021 | 9/1982 | Boyd et al. | 378/12 |
| 4,472,737 | 9/1984 | Iwasaki | 358/111 |
| 4,539,639 | 9/1985 | Le Coq et al. | 378/901 |
| 4,573,179 | 2/1986 | Rutt | 378/10 |

Primary Examiner—Janice A. Howell
Attorney, Agent, or Firm—Flehr, Hohbach, Test, Albritton & Herbert

[57] ABSTRACT

A stereoscopic or three dimensional radiograph or a continuously rotating three dimensional radiograph of a patient is obtained using a high speed CT scanning system in which fan beams of radiation are generated by sweeping an electron beam along a target. Collimated X-rays emitted by the target are received by an array of detectors after passing through a patient area between the target and the array of detectors. Two detector positions, comprising one or more detectors, each can be employed to obtain a pair of two dimensional projection radiographs. The radiographs are alternately viewed by a viewer by selectively opening and closing shutter means associated with the eyes of the viewer as the radiographs are alternately assembled for viewing whereby one eye sees one radiograph and the other eye sees the other radiograph. Alternatively, a plurality of pairs of detector positions can be employed in measuring radiation and obtaining a continuously rotating three dimensional projection radiograph.

6 Claims, 4 Drawing Figures

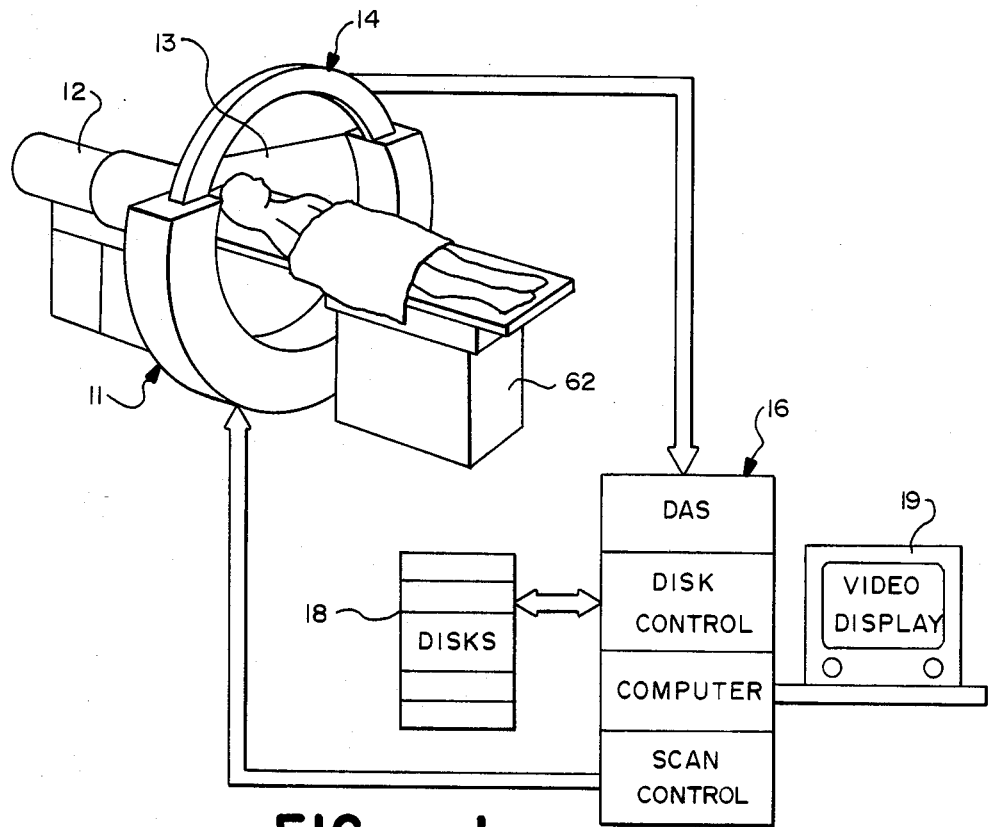
FIG.—1
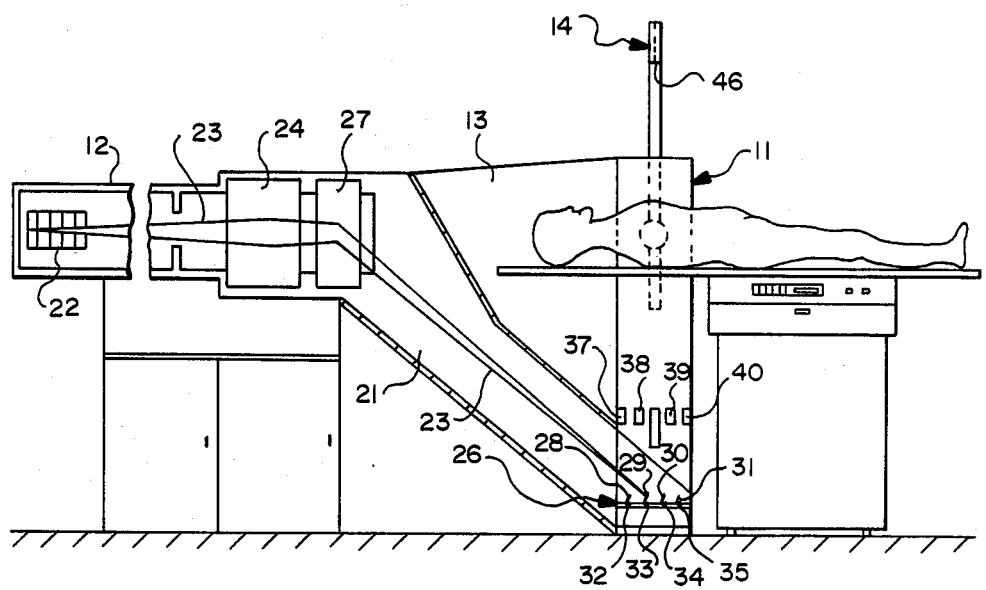
FIG.—2

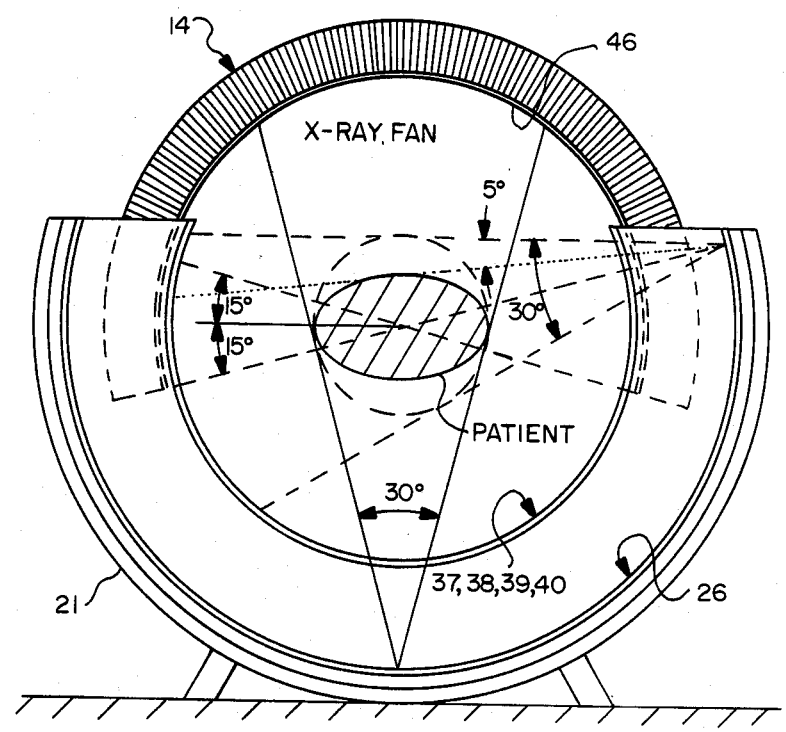
FIG.—3
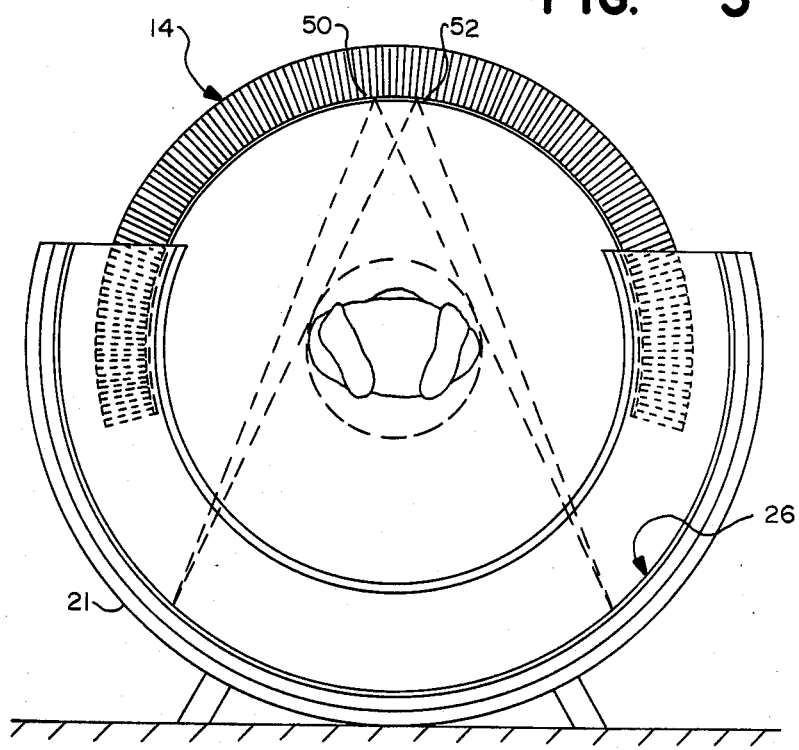
FIG.—4

THREE DIMENSIONAL SCANNED PROJECTION RADIOGRAPHY USING HIGH SPEED COMPUTED TOMOGRAPHIC SCANNING SYSTEM

This invention relates generally to a high speed multiple section computed-tomographic (CT) medical scanning system, and more particularly the invention relates to a method of scanned projection radiography using such a scanning system.

Disclosed in U.S. Pat. No. 4,352,021 is a high speed X-ray scanning system in which the X-ray source and the X-ray detectors are stationary and a plurality of fan beams of radiation is generated by sweeping an electron beam across a plurality of targets accurately arranged whereby each target generates radiation fan beams. Such a system is now commercially available from Imatron, Inc., assignee of the present application.

The electronic scanning system incorporates a single electron beam tube. The electron beam is deflected by suitable magnetic and/or electric fields to produce a movable X-ray source on one of four adjacent semi-circular target rings to provide scanning fan beams that can be used to image an entire volume of tissue in multiple sections. Such an electronic scanning system is vastly superior in speed to prior art mechanical scanning systems such as disclosed in U.S. Pat. No. 4,075,492. Fraction-of-a-second scan time of a volume can be achieved as compared to one or more seconds required for the mechanical scan of a single section. The system eliminates the need for moving parts that require high precision end alignment. In addition, elaborate systems of sliding electrical contacts are eliminated. The scanner is an improvement over that shown and described in U.S. Pat. No. 4,158,142 in that it permits nearly simultaneous viewing multiple sections of the body which may encompass a region as large as the heart. The scanner can provide as many as eight sections.

The system employs a plurality of detectors mounted opposite the target rings. The detectors are arranged in two adjacent partial-circular ring arrays. Each of the arrays contains a multiplicity of detectors as, for example, 444 detectors each, providing a total of 888 detectors. The angular separation of two adjacent detectors is in the order of 0.5 degrees resulting in very high resolution. The scanning system is provided with collimators both for the X-ray source and for the detectors. The source collimators comprise brass rings along with the detector housing which cooperatively define a plurality of fan beams. The detector collimators provide interchangeable options: dual section detector arrays, single section detector arrays and high resolution single section detector arrays. A variety of scanning modes can be selected with up to eight sections being scanned at a rate of at least one scan per second.

Disclosed in copending application Ser. No. 615,063, filed May 29, 1984, now U.S. Pat. No. 4,573,179, for "Scanned Projection Radiography Using High Speed Computed Tomographic Scanning System", now U.S. Pat. No. 4,573,179 assigned to the present assignee, is a method of generating a two dimensional projection radiographic using the described high speed CT scanning system. Radiation measurements are made at a single detector position as the electron beam is swept along the target track and the patient is moved through the collimated fan beam of radiation. Alternatively, a plurality of detector positions can be used for obtaining projection data whereby the patient can be viewed from any angle within the angle of the detector array or a continuously rotating two dimensional radiographic image is obtained.

U.S. Pat. No. 4,573,179 is hereby incorporated by reference.

The present invention is related to the scanned projection radiography disclosed in the copending application and issued U.S. Pat. No. 4,573,179. More particularly, a three dimensional or stereoscopic projection image is produced by generating projection radiography data at two closely spaced detector positions and using the data from the two positions for generating two alternating images such as alternate frames in a video monitor. Monitoring means is provided whereby the viewer sees one image with one eye and the other image with the other eye thereby allowing the viewer to perceive a three dimensional or stereoscopic image.

Accordingly, an object of the invention is a method of viewing a stereoscopic projection radiograph.

A feature of the invention is the collection of data representing two dimensional projected radiographs which are selectively viewed by the eyes of the viewer.

The invention and objects and features thereof will be more readily apparent from the following detailed description and appended claims when taken with the drawing, in which:

FIG. 1 is a schematic diagram partly in perspective showing a computed tomographic X-ray transmission scanning system employing multiple electron beam targets.

FIG. 2 is a cross section view of the system of FIG. 1.

FIG. 3 is an end view of the system of FIG. 1.

FIG. 4 is an end view of the system of FIG. 1 illustrating use thereof in obtaining stereoscopic projection data in accordance with the invention.

Referring now to FIG. 1, the system of U.S. Pat. No. 4,352,021 is seen to include three major components: a scan tube 11 including a cylindrical portion 12, and a semicircular conical portion 13; a detector array 14; and, a computer system 16. The scan tube projects an electron beam to target rings which generate X-rays. The X-rays are intercepted by the detector array 14. The output of the detector array is applied to the computer system 16. The computer system includes a plurality of storage discs 18 for recording the data for later processing. The computer system also includes an output which controls the scan tube. A video display 19 presents the data.

Referring more particularly to FIGS. 2 and 3, the scanning system and detection system are shown in more detail. The electron beam tube 11 includes a vacuum envelope 21 which houses an electron gun 22 at the cylindrical end 12. The electron gun projects an axial electron beam 23 along the cylindrical portion. The focus coils 24 focus the beam onto targets 26. Bending coils 27 bend the beam so that it moves along the partial-circular conical portion of the tube to impinge upon the partial-circular target rings. The target assembly 26 includes a plurality of partial-circular target rings 28, 29, 30 and 31. Suitable cooling coils 32, 33, 34 and 35 are associated with each of the target rings 28, 29, 30 and 31 respectively and serve to cool the target rings. The bending magnets not only deflect the beam but rapidly sweep it along the partial-circular targets shown in FIGS. 2 and 3. The target rings are scanned serially to obtain a multiple section examination as will be presently described. Ring collimators 37, 38, 39 and 40 are disposed to intercept X-rays emitted by the target rings and define an X-ray beam projected as a one or two centimeter thick planar beam. A fan-shaped sector of this beam is detected by the curved detector array and the measured values are utilized to reconstruct a tomographic image.

The detector array is in the form of a ring which overlaps the ring collimators. In the overlapping region the detector fits between the second and third collimator rings 38 and 39. The detector array 14 likewise may extend as much as 210° and is semicircular. A suitable detector collimator 46 serves to pass the X-rays to the associated detector. Overlap of the source and detector rings assures that at least 180° of projection data can be obtained.

The reconstruction region is indicated by the dotted circle 44, FIG. 3, and has a diameter of approximately 50 centimeters. For oval-shaped patients such as indicated by the shaded region, more than 190° of projection data can be obtained. The degree of overscanning increases to about 230° for posterior regions. Overscan is known to be an important feature of CT scanning that can be used to reduce streak artifacts due to data inconsistencies at 0° and 180°. The rays that pass outside the reconstruction circle are used to calibrate the individual detectors in the stationary array.

As disclosed in copending application Ser. No. 615,063, now U.S. Pat. No. 4,573,179 supra, a projection radiograph is obtained with the described high speed scanner by using the output of a single detector position as the electron beam is swept along a single target track repeatedly and the patient is moved linearly past the collimated beam. In accordance with the present invention projection radiograph data is obtained at two closely spaced detector positions 50 and 52 as shown in FIG. 4 of the drawing. The spacing between the two detector positions should correspond essentially to the spacing between the eyes of a viewer. The data from each detector position 50, 52 is then utilized to generate an image of the radiogram. For example, the two images may comprise alternate frames in a video display. The two frames are projected at a sufficient rate (e.g. 60 frames per second) so that the viewer does not detect flicker in either image. Suitable viewing means such as a stereo viewer is then employed to allow each eye to view only one frame of the projected images. Such a viewer is disclosed by Roese et al, "Single Monitor Stereoradiological Television System Using PLXT Electrooptic Shutters", *Radiology* 121: 743-744, December 1976 and in U.S. Pat. No. 4,214,267 for Sterofluoroscopy System. Accordingly, a stereoscopic or three dimensional radiograph is then perceived by the viewer. Moreover, the stereoscopic radiograph permits smooth and rapid transitions from one angular view to the next thereby giving the impression of a continuous or real time rotation of a three dimensional projection view of the patient. This is accomplished by sequentially using a plurality of pairs of detector positions.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. In a high speed CT scanning system in which fan beams of radiation are generated by sweeping an electron beam along a target and collimated X-rays emitted by the target are received by an array of detectors after passing through a patient area between said target and said array of detectors, a method of obtaining a stereoscopic radiographic of a patient comprising the steps of
   sweeping said electron beam along said target,
   measuring radiation received at two detector positions as said electron beam is swept along said target,
   moving said patient past said collimated X-rays, and
   assembling two radiographs from said radiation measured at said two detector positions, said two radiographs being alternately viewed by a viewer.

2. The method as defined by claim 1 wherein said two radiographs are alternatively viewed by a viewer by selectively opening and closing shutter means associated with the eyes of the viewer as said radiographs are alternately assembled for viewing such that one eye sees one radiograph and the other eye sees the other radiograph.

3. The method as defined by claim 2 wherein said step of measuring radiation includes measuring radiation with a single pair of detectors.

4. The method as defined by claim 2 wherein said step of measuring radiation includes measuring radiation with a plurality of detectors and generating a single measurement using measurements from said plurality of detectors.

5. The method as defined by claim 2 and further including the steps of measuring radiation received at at least two other detector positions while moving said patient past said collimated X-rays, and
   assembling at least one other pair of two dimensional radiographs from said radiation measured at said at least two other detector positions.

6. The method as defined by claim 5 wherein said step of measuring radiation includes sequential measurements of radiation at a plurality of pairs of other detector positions, and said step of assembling radiographs include assembling a radiograph for each pair of other detectors such that a rotational stereoscopic image is obtained.

* * * * *